United States Patent
Pohl et al.

(10) Patent No.: US 9,200,048 B2
(45) Date of Patent: Dec. 1, 2015

(54) HIGH ACTIVITY GROWTH FACTOR MUTANTS

(71) Applicant: Biopharm Gesellschaft zur biotechnologischen Entwicklung von Pharmaka mbH, Heidelberg (DE)

(72) Inventors: Jens Pohl, Hambruecken (DE); Frank Ploeger, Heidelberg (DE); Michael Kruse, Mainz (DE)

(73) Assignee: Biopharm Gesellschaft zur biotechnologischen Entwicklung von Pharmaka mbH, Heidelberg (DE)

( * ) Notice: Subject to any disclaimer, the term of this patent is extended or adjusted under 35 U.S.C. 154(b) by 0 days.

(21) Appl. No.: 14/182,604

(22) Filed: Feb. 18, 2014

(65) Prior Publication Data

US 2015/0057223 A1 Feb. 26, 2015

Related U.S. Application Data

(60) Continuation of application No. 13/457,957, filed on Apr. 27, 2012, now abandoned, which is a division of application No. 12/094,227, filed as application No. PCT/EP2006/011074 on Nov. 17, 2006, now Pat. No. 8,188,226.

(30) Foreign Application Priority Data

Nov. 18, 2005 (EP) .................... 05025261

(51) Int. Cl.
*C07K 14/495* (2006.01)
*C07K 14/475* (2006.01)
*A61K 38/00* (2006.01)

(52) U.S. Cl.
CPC ............ *C07K 14/495* (2013.01); *C07K 14/475* (2013.01); *A61K 38/00* (2013.01)

(58) Field of Classification Search
None
See application file for complete search history.

(56) References Cited

U.S. PATENT DOCUMENTS

| 5,013,649 | A | 5/1991 | Wang et al. |
| 6,972,321 | B1 | 12/2005 | Hoetten |
| 2004/0009916 | A1 | 1/2004 | Wang et al. |

FOREIGN PATENT DOCUMENTS

| EP | 1 074 620 A | 2/2001 |
| EP | 1 439 190 A | 7/2004 |
| WO | 94/15949 A1 | 7/1994 |
| WO | 95/16035 A2 | 6/1995 |
| WO | 97/33215 A2 | 9/1997 |
| WO | 99/15191 A2 | 4/1999 |
| WO | WO 00/21998 A | 4/2000 |
| WO | 01/11041 A1 | 2/2001 |
| WO | 02/076494 A2 | 10/2002 |
| WO | 2006/023520 A2 | 3/2006 |

OTHER PUBLICATIONS van Lierop et al. Patients with sclerosteosis and disease carriers: human models of the effect of sclerostin on bone turnover. J Bone Miner Res. Dec. 2011;26(12):2804-11.*
Storm EE, Kingsley DM. GDF5 coordinates bone and joint formation during digit development. Dev Biol. May 1, 1999;209(1):11-27.*
Seemann et al., "Activating and deactivating mutations in the receptor interaction site of GDF5 cause symphalangism or brachydactyly type A2", Journal of Clinical Investigation, vol. 115, No. 9, Sep. 2005, pp. 2373-2381.
Kulessa et al., "Inhibition of Bmp signaling affects growth and differentiation in the anagen hair follicle", EMBO Journal, vol. 19, No. 24, Dec. 15, 2000, pp. 6664-6674.
Ducy et al., "The family of bone morphogenetic proteins", Kidney International, vol. 57, No. 6, Jun. 2000, pp. 2207-2214.
Storm et al., "Limb alternations in brachypodism mice due to mutations in a new member of the TGFbeta-superfamily", Nature, vol. 368, Apr. 14, 1994, pp. 639-643.
Rui et al., "Protein Engineering of Expoxide Hydrolase from Agrobacterium radiobacter AD1 for Enhanced Activity and Enantioselective Production of (R)-1-Phenylethane-1, 2-Diol", Applied and Environmental Microbiology, Jul. 2005, vol. 71, No. 7, pp. 3995-4003.
Guo et al., "Protein Tolerance to Random Amino Acid Change", Proc Natl Acad Sci USA, Jun. 22, 2004: 101(25), pp. 9205-9210, Epub Jun. 14, 2004.
Ngo et al., The Protein Folding Problem and Tertiary Structure Prediction, Merz and Le Grand (Eds) , Aug. 1994, Springer Verlag, pp. 433 and 492-495.
Sanchez-Capelo et al., Adenovirus-Mediated Over-Expression of TGFβ1 in the Striatum Decreases Dopaminergic Cell Curvival in Embryonic Nigral Grafts, Neuroreport, Jul. 13, 1999; 10(10), pp. 2169-2173.
Sun et al., "The Cystine-Knot Growth-Factor Superfamily", Annu Rev Biophys Biomol Struct, 1995, 24, pp. 269-291.
Umlauf et al., "Cartilage Biology, Pathology, and Repair", Cell Mol Life Science, Dec. 2010, 67 (24), pp. 4197-41211, Epub. Aug. 25, 2010.
Vickers J.C. "A vaccine against Alzheimer's disease: developments to date", Drugs & Aging, 2002, 19(7), pp. 487-494.
Wozney et al., "Novel Regulators of Bone Formation: Molecular Clones and Activities", Science, vol. 242, 1988, pp. 1528-1534.
Betts, M.J. and Russell, R.B., "Amino Acid Properties and Consequences of Substitutions", Chapter 14, Bioinformatics for Geneticists (2003), John Wiley & Sons, Ltd.
Yamaguchi et al., Regulation of Osteoblast Differentiation Mediated by Bone Morphogenetic Proteins, Hedgehogs and Cbfa1; Endocrine Reviews 21(4): 393-411 (2000).

* cited by examiner

*Primary Examiner* — David Romeo
(74) *Attorney, Agent, or Firm* — Rothwell, Figg, Ernst & Manbeck, P.C.

(57) ABSTRACT

The invention relates to novel biosynthetic growth factor mutants which exhibit improved biological activity.

12 Claims, 7 Drawing Sheets

FIG. 1

```
  1 MRLPKLLTFL LWYLAWLDLE FICTVLGAFD LGQRPQGTRP GLAKAEAKER PPLARNVFRP

61 GGHSYGGGAT NANARAKGGT GQTGGLTQPK KDEPKKLPPR PGGPEPKPGH PPQTRQATAR

121 TVTPKGQLPG GKAPPKAGSV PSSFLLKKAR EPGPPREPKE PFRPPPITPH EYMLSLYRTL

181 SDADRKGGNS SVKLEAGLAN TITSFIDKGQ DDRGPVVRKQ RYVFDISALE KDGLLGAELR

241 ILRKKPSDTA KPAAPGGGRA AQLKLSSCPS GRQPASLLDV RSVPGLDGSG WEVFDIWKLF

301 RNFKNSAQLC LELEAWERGR AVDLRGLGFD RAARQVHEKA LFLVFGRTAK RDLFFNEIKA

361 RSGQDDKTVY EYLFSQRRKR RAPLATRQGK RPSKNLKARC SRKALHVNFK DMGWDDWIIA

421 PLEYEAFHCE GLCEFPLRSH LEPTNHAVIQ TLMNSMDPES TPPTCCVPTR LSPISILFID

481 SANNVVYKQY EDMVVESCGC R
```

FIG. 2

```
                                                                    M453 M456  (hGDF-5)
                                                                      ↓    ↓
hGDF-6 : CSKRPLHVNFKELGWDDWIIAPLEYEAYHCEGVCDFPIRSHLEPTNHAIIQTLMNSMDPGSTEPSCCVPTKLTPISILYIDAGNNVV  :  87
hGDF-7 : CSRRPLHVDFKELGWDDWIIAPLDYEAYHCEGLCDFPIRSHLEPTNHAIIQTLLNSMAPDAAPASCCVPARLSPISILYIDAANNVV  :  87
hGDF-5 : CSRRALHVNFKDMGWDDWIIAPLEYEAFHCEGLCEFPIRSHLEPTNHAVIQTLMNSMDPESTLPTCCVPTRLSPISILFIDSANNVV  :  87 hGDF-6 : YKQYEDMVVESCGCR
hGDF-7 : YKQYEDMVVEACGCR
hGDF-5 : YKQYEDMVVESCGCR
```

FIG. 4

% sequence identity to
cystine-knot-domain of human GDF-5

| Sequence | % Identity | Identical Residues |
|---|---|---|
| GDF-5 Homo | 100 | 102/102 |
| GDF-5 Mus | 99 | 101/102 |
| GDF-5 Gallus | 99 | 101/102 |
| GDF-5 Xenopus | 94 | 96/102 |
| GDF-5 Danio (Contact) | 88 | 90/102 |
| GDF-7 Danio | 88 | 90/102 |
| GDF-6 Mus | 86 | 88/102 |
| GDF-7 Gallus | 86 | 88/102 |
| GDF-6 Danio (Radar) | 86 | 88/102 |
| GDF-6 Homo | 85 | 87/102 |
| GDF-6 Xenopus | 84 | 86/102 |
| GDF-6 Bos | 83 | 85/102 |
| GDF-7 Homo | 81 | 83/102 |
| GDF-7 Cercopithecus | 80 | 82/102 |
| GDF-7 Macaca | 80 | 82/102 |
| GDF-7 Mus | 80 | 82/102 |
| GDF-6 Danio (Dynamo) | 79 | 81/102 |
| BMP-2A | 57 | 58/102 |
| BMP-2B | 57 | 58/102 |
| Vg-1 | 52 | 53/102 |
| DPP | 52 | 53/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| 60A | 48 | 49/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/102 |
| GDF-12 | 37 | 38/104 |
| GDF-11 | 36 | 37/102 |
| GDF-9 | 32 | 33/102 |

New Bone Formation

Estimated amount of new bone formation on the scaffolds by using following scaling:

no      bone    → 0
     1- 10 %  bone    → 1
     10- 50 % bone    → 2
     50-100% bone     → 3

|  | rhGDF-5 | rhGDF-5 M453V/M456V | BMP-2 | Control |
|---|---|---|---|---|
| Mean Value (n=3) | 0,94 | 2,78 | 1,89 | 0 |
| SD | 0,48 | 0,10 | 0,35 | 0 |

SEQUENCE LISTING

```
<160> NUMBER OF SEQ ID NOS: 24

<210> SEQ ID NO 1
<211> LENGTH: 501
<212> TYPE: PRT
<213> ORGANISM: Homo sapiens

<400> SEQUENCE: 1

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175
```

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 2
<211> LENGTH: 2703
<212> TYPE: DNA
<213> ORGANISM: Homo sapiens

<400> SEQUENCE: 2
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta     240

```
gggggaaaaa aaaactggag cacacaggca gcattacgcc attcttcctt cttggaaaaa    300
tccctcagcc ttatacaagc ctccttcaag ccctcagtca gttgtgcagg agaaaggggg    360
cggttggctt tctcctttca agaacgagtt attttcagct gctgactgga gacggtgcac    420
gtctggatac gagagcattt ccactatggg actggataca acacacacc cggcagactt     480
caagagtctc agactgagga gaaagccttt ccttctgctg ctactgctgc tgccgctgct    540
tttgaaagtc cactccttc atggttttc ctgccaaacc agaggcacct ttgctgctgc      600
cgctgttctc tttggtgtca ttcagcggct ggccagagga tgagactccc caaactcctc    660
actttcttgc tttggtacct ggcttggctg gacctggaat tcatctgcac tgtgttgggt    720
gcccctgact tgggccagag accccagggg accaggccag gattggccaa agcagaggcc    780
aaggagaggc cccccctggc ccggaacgtc ttcaggccag ggggtcacag ctatggtggg    840
ggggccacca atgccaatgc cagggcaaag ggaggcaccg gcagacagg aggcctgaca     900
cagcccaaga aggatgaacc caaaaagctg ccccccagac cgggcggccc tgaacccaag    960
ccaggacacc ctccccaaac aaggcaggct acagcccgga ctgtgacccc aaaaggacag   1020
cttcccggag gcaaggcacc cccaaaagca ggatctgtcc ccagctcctt cctgctgaag   1080
aaggccaggg agcccgggcc cccacgagag cccaaggagc cgtttcgccc accccccatc   1140
acacccccacg agtacatgct ctcgctgtac aggacgctgt ccgatgctga cagaaaggga   1200
ggcaacagca gcgtgaagtt ggaggctggc ctggccaaca ccatcaccag ctttattgac   1260
aaagggcaag atgaccgagg tcccgtggtc aggaagcaga ggtacgtgtt tgacattagt   1320
gccctggaga aggatgggct gctggggggcc gagctgcgga tcttgcggaa gaagccctcg   1380
gacacggcca agccagcggc cccggaggc gggcgggctg cccagctgaa gctgtccagc    1440
tgccccagcg gccggcagcc ggcctccttg ctggatgtgc gctccgtgcc aggcctggac   1500
ggatctggct gggaggtgtt cgacatctgg aagctcttcc gaaactttaa gaactcggcc   1560
cagctgtgcc tggagctgga ggcctgggaa cggggcaggg ccgtggacct ccgtggcctg   1620
ggcttcgacc gcgccgcccg gcaggtccac gagaaggccc tgttcctggt gtttggccgc   1680
accaagaaac gggacctgtt ctttaatgag attaaggccc gctctggcca ggacgataag   1740
accgtgtatg agtacctgtt cagccagcgg cgaaaacggc gggcccccact ggccactcgc   1800
cagggcaagc gacccagcaa gaaccttaag gctcgctgca gtcggaaggc actgcatgtc   1860
aacttcaagg acatgggctg ggacgactgg atcatcgcac cccttgagta cgaggctttc   1920
cactgcgagg ggctgtgcga gttcccattg cgctcccacc tggagcccac gaatcatgca   1980
gtcatccaga ccctgatgaa ctccatggac cccgagtcca caccacccac ctgctgtgtg   2040
cccacgcggc tgagtcccat cagcatcctc ttcattgact ctgccaacaa cgtggtgtat   2100
aagcagtatg aggacatggt cgtggagtcg tgtggctgca ggtagcagca ctggccctct   2160
gtcttcctgg gtggcacatc ccaagagccc cttcctgcac tcctgaatc acagaggggt    2220
caggaagctg tggcaggagc atctacacag cttgggtgaa aggggattcc aataagcttg   2280
ctcgctctct gagtgtgact tgggctaaag gccccttttt atccacaagt tccctggct   2340
gaggattgct gcccgtctgc tgatgtgacc agtggcagga caggtccag ggagacagac     2400
tctgaatggg actgagtccc aggaaacagt gctttccgat gagactcagc ccaccatttc   2460
tcctcacctg ggccttctca gcctctggac tcctcaagc acctcagg agagccacag     2520
gtgccactgc ctcctcaaat cacatttgtg cctggtgact tcctgtccct gggacagttg   2580
```

```
agaagctgac tgggcaagag tgggagagaa gaggagaggg cttggataga gttgaggagt    2640
gtgaggctgt tagactgtta gatttaaatg tatattgatg agataaaaag caaaactgtg    2700
cct                                                                  2703
```

```
<210> SEQ ID NO 3
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P),
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES ALANINE(A), ISOLEUCINE(I), OR
      VALINE(V)
```

```
<220> FEATURE:
<221> NAME/KEY: MISC_FEATURE
<222> LOCATION: (58)..(58)
<223> OTHER INFORMATION: X DENOTES ALANINE(A), ASPARAGINE(N), OR
      ASPARTIC ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S), OR
      THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S)
      OR THREONINE(T)

<400> SEQUENCE: 3

Cys Xaa Xaa Lys Xaa Leu His Val Xaa Phe Xaa Xaa Xaa Gly Trp Asp
1               5                   10                  15
```

-continued

```
Asp Trp Xaa Ile Ala Pro Leu Xaa Tyr Glu Ala Xaa His Cys Xaa Gly
            20                  25                  30

Xaa Cys Xaa Phe Pro Xaa Arg Ser His Leu Glu Pro Thr Asn His Ala
        35                  40                  45

Xaa Ile Gln Thr Leu Xaa Asn Ser Met Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
            100
```

<210> SEQ ID NO 4
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P)
    OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F), OR
    TYROSINE(Y)
<220> FEATURE:
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M), OR
    VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)

```
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (57)..(57)
<223> OTHER INFORMATION: X DENOTES ALANINE(A), ISOLEUCINE(I) OR
      VALINE(V)
<220> FEATURE:
<221> NAME/KEY: MISC_FEATURE
<222> LOCATION: (58)..(58)
<223> OTHER INFORMATION: X DENOTES ALANINE(A), ASPARAGINE(N) OR ASPARTIC
      ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S),
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M), OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S) OR THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
```

<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S),
      OR THREONINE(T)

<400> SEQUENCE: 4

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Ser His Leu Glu Pro Thr Asn His Ala
        35                  40                  45

Xaa Ile Gln Thr Leu Met Asn Ser Xaa Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
            85                  90                  95

Glu Xaa Cys Gly Cys Arg
            100

<210> SEQ ID NO 5
<211> LENGTH: 102
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X DENOTES ASPARAGINE(N) OR SERINE(S)
<220> FEATURE:
<221> NAME/KEY: MISC_FEATURE
<222> LOCATION: (3)..(3)
<223> OTHER INFORMATION: X DENOTES ARGININE(R) OR LYSINE(K)
<220> FEATURE:
<221> NAME/KEY: MISC_FEATURE
<222> LOCATION: (5)..(5)
<223> OTHER INFORMATION: X DENOTES ALANINE(A), GLUTAMINE(Q), PROLINE(P)
      OR SERINE(S)
<220> FEATURE:
<221> NAME/KEY: MISC_FEATURE
<222> LOCATION: (9)..(9)
<223> OTHER INFORMATION: X DENOTES ASPARAGINE(N) OR ASPARTIC ACID(D)
<220> FEATURE:
<221> NAME/KEY: MISC_FEATURE
<222> LOCATION: (11)..(11)
<223> OTHER INFORMATION: X DENOTES ARGININE(R) OR LYSINE(K)
<220> FEATURE:
<221> NAME/KEY: MISC_FEATURE
<222> LOCATION: (12)..(12)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (13)..(13)
<223> OTHER INFORMATION: X DENOTES LEUCINE(L) OR METHIONINE(M)
<220> FEATURE:
<221> NAME/KEY: MISC_FEATURE
<222> LOCATION: (19)..(19)
<223> OTHER INFORMATION: X DENOTES ISOLEUCINE(I) OR VALINE(V)
<220> FEATURE:
<221> NAME/KEY: MISC_FEATURE
<222> LOCATION: (24)..(24)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (28)..(28)
<223> OTHER INFORMATION: X DENOTES HISTIDINE(H), PHENYLALANINE(F) OR
      TYROSINE(Y)
<220> FEATURE:

```
<221> NAME/KEY: MISC_FEATURE
<222> LOCATION: (31)..(31)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (33)..(33)
<223> OTHER INFORMATION: X DENOTES LEUCINE(L), METHIONINE(M) OR
      VALINE(V)
<220> FEATURE:
<221> NAME/KEY: MISC_FEATURE
<222> LOCATION: (35)..(35)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (38)..(38)
<223> OTHER INFORMATION: X DENOTES ISOLEUCINE(I) OR LEUCINE(L)
<220> FEATURE:
<221> NAME/KEY: MISC_FEATURE
<222> LOCATION: (49)..(49)
<223> OTHER INFORMATION: X DENOTES ISOLEUCINE(I) OR VALINE(V)
<220> FEATURE:
<221> NAME/KEY: MISC_FEATURE
<222> LOCATION: (54)..(54)
<223> OTHER INFORMATION: X DENOTES ALANINE(A), ISOLEUCINE(I) OR
      VALINE(V)
<220> FEATURE:
<221> NAME/KEY: MISC_FEATURE
<222> LOCATION: (57)..(57)
<223> OTHER INFORMATION: X DENOTES ALANINE(A), ISOLEUCINE(I) OR
      VALINE(V)
<220> FEATURE:
<221> NAME/KEY: MISC_FEATURE
<222> LOCATION: (58)..(58)
<223> OTHER INFORMATION: X DENOTES ALANINE(A), ASPARAGINE(N) OR ASPARTIC
      ACID(D)
<220> FEATURE:
<221> NAME/KEY: MISC_FEATURE
<222> LOCATION: (60)..(60)
<223> OTHER INFORMATION: X DENOTES ARGININE(R), ASPARAGINE(N), ASPARTIC
      ACID(D), GLUTAMIC ACID(E), GLYCINE(G), OR SERINE(S)
<220> FEATURE:
<221> NAME/KEY: MISC_FEATURE
<222> LOCATION: (61)..(61)
<223> OTHER INFORMATION: X DENOTES ALANINE(A), ASPARAGINE(N), SERINE(S)
      OR THREONINE(T)
<220> FEATURE:
<221> NAME/KEY: MISC_FEATURE
<222> LOCATION: (62)..(62)
<223> OTHER INFORMATION: X DENOTES ALANINE(A), METHIONINE(M) OR
      THREONINE(T)
<220> FEATURE:
<221> NAME/KEY: MISC_FEATURE
<222> LOCATION: (64)..(64)
<223> OTHER INFORMATION: X DENOTES ALANINE(A) OR PROLINE(P)
<220> FEATURE:
<221> NAME/KEY: MISC_FEATURE
<222> LOCATION: (65)..(65)
<223> OTHER INFORMATION: X DENOTES SERINE(S) OR THREONINE(T)
<220> FEATURE:
<221> NAME/KEY: MISC_FEATURE
<222> LOCATION: (70)..(70)
<223> OTHER INFORMATION: X DENOTES ALANINE(A), SERINE(S) OR THREONINE(T)
<220> FEATURE:
<221> NAME/KEY: MISC_FEATURE
<222> LOCATION: (71)..(71)
<223> OTHER INFORMATION: X DENOTES ARGININE(R) OR LYSINE(K)
<220> FEATURE:
<221> NAME/KEY: MISC_FEATURE
<222> LOCATION: (73)..(73)
<223> OTHER INFORMATION: X DENOTES SERINE(S) OR THREONINE(T)
<220> FEATURE:
<221> NAME/KEY: MISC_FEATURE
<222> LOCATION: (79)..(79)
<223> OTHER INFORMATION: X DENOTES PHENYLALANINE(F) OR TYROSINE(Y)
<220> FEATURE:
<221> NAME/KEY: MISC_FEATURE
<222> LOCATION: (80)..(80)
<223> OTHER INFORMATION: X DENOTES ISOLEUCINE(I) OR THREONINE(T)
<220> FEATURE:
```

```
<221> NAME/KEY: MISC_FEATURE
<222> LOCATION: (82)..(82)
<223> OTHER INFORMATION: X DENOTES ALANINE(A) OR SERINE(S)
<220> FEATURE:
<221> NAME/KEY: MISC_FEATURE
<222> LOCATION: (83)..(83)
<223> OTHER INFORMATION: X DENOTES ALANINE(A) OR GLYCINE(G)
<220> FEATURE:
<221> NAME/KEY: MISC_FEATURE
<222> LOCATION: (89)..(89)
<223> OTHER INFORMATION: X DENOTES ASPARAGINE(N) OR LYSINE(K)
<220> FEATURE:
<221> NAME/KEY: MISC_FEATURE
<222> LOCATION: (90)..(90)
<223> OTHER INFORMATION: X DENOTES GLUTAMIC ACID(E) OR GLUTAMINE(Q)
<220> FEATURE:
<221> NAME/KEY: MISC_FEATURE
<222> LOCATION: (93)..(93)
<223> OTHER INFORMATION: X DENOTES ASPARTIC ACID(D) OR GLUTAMIC ACID(E)
<220> FEATURE:
<221> NAME/KEY: MISC_FEATURE
<222> LOCATION: (98)..(98)
<223> OTHER INFORMATION: X DENOTES ALANINE(A), GLUTAMINE(Q), SERINE(S),
      OR THREONINE(T)

<400> SEQUENCE: 5

Cys Xaa Xaa Lys Xaa Leu His Val Xaa Phe Xaa Xaa Xaa Gly Trp Asp
1               5                   10                  15

Asp Trp Xaa Ile Ala Pro Leu Xaa Tyr Glu Ala Xaa His Cys Xaa Gly
            20                  25                  30

Xaa Cys Xaa Phe Pro Xaa Arg Ser His Leu Glu Pro Thr Asn His Ala
        35                  40                  45

Xaa Ile Gln Thr Leu Xaa Asn Ser Xaa Xaa Pro Xaa Xaa Xaa Pro Xaa
    50                  55                  60

Xaa Cys Cys Val Pro Xaa Xaa Leu Xaa Pro Ile Ser Ile Leu Xaa Xaa
65                  70                  75                  80

Asp Xaa Xaa Asn Asn Val Val Tyr Xaa Xaa Tyr Glu Xaa Met Val Val
                85                  90                  95

Glu Xaa Cys Gly Cys Arg
        100

<210> SEQ ID NO 6
<211> LENGTH: 102
<212> TYPE: PRT
<213> ORGANISM: Homo sapiens

<400> SEQUENCE: 6

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Ile Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
        100

<210> SEQ ID NO 7
```

```
<211> LENGTH: 102
<212> TYPE: PRT
<213> ORGANISM: Homo sapiens

<400> SEQUENCE: 7

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Ile Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 8
<211> LENGTH: 102
<212> TYPE: PRT
<213> ORGANISM: Homo sapiens

<400> SEQUENCE: 8

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 9
<211> LENGTH: 102
<212> TYPE: PRT
<213> ORGANISM: Mus musculus

<400> SEQUENCE: 9

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80
```

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 10
<211> LENGTH: 102
<212> TYPE: PRT
<213> ORGANISM: Gallus gallus

<400> SEQUENCE: 10

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Tyr His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 11
<211> LENGTH: 102
<212> TYPE: PRT
<213> ORGANISM: Danio rerio

<400> SEQUENCE: 11

Cys Asn Arg Lys Gln Leu His Val Asn Phe Lys Glu Met Gly Trp Asp
1               5                   10                  15

Asp Trp Ile Ile Ala Pro Leu Glu Tyr Glu Ala Phe His Cys Asp Gly
            20                  25                  30

Val Cys Asp Phe Pro Ile Arg Ser His Leu Glu Pro Thr Asn His Ala
        35                  40                  45

Ile Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Tyr Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 12
<211> LENGTH: 102
<212> TYPE: PRT
<213> ORGANISM: Xenopus laevis

<400> SEQUENCE: 12

Cys Ser Lys Lys Pro Leu His Val Asn Phe Lys Asp Met Gly Trp Asp
1               5                   10                  15

Asp Trp Ile Ile Ala Pro Leu Glu Tyr Glu Ala Tyr His Cys Glu Gly
            20                  25                  30

Leu Cys Glu Phe Pro Leu Arg Ser His Leu Glu Pro Thr Asn His Ala

```
                35                  40                  45
Val Ile Gln Thr Leu Met Asn Ser Met Asp Pro Glu Thr Thr Pro Pro
 50                  55                  60

Thr Cys Cys Val Pro Thr Arg Leu Ser Pro Ile Ser Ile Leu Tyr Thr
 65                  70                  75                  80

Asp Ser Ala Asn Asn Val Val Tyr Lys Gln Tyr Glu Asp Met Val Val
                 85                  90                  95

Glu Ser Cys Gly Cys Arg
                100

<210> SEQ ID NO 13
<211> LENGTH: 102
<212> TYPE: PRT
<213> ORGANISM: Homo sapiens

<400> SEQUENCE: 13

Cys Ser Lys Lys Pro Leu His Val Asn Phe Lys Glu Leu Gly Trp Asp
 1               5                  10                  15

Asp Trp Ile Ile Ala Pro Leu Glu Tyr Glu Ala Tyr His Cys Glu Gly
                 20                  25                  30

Leu Cys Glu Phe Pro Leu Arg Ser His Leu Glu Pro Thr Asn His Ala
             35                  40                  45

Ile Ile Gln Thr Leu Met Asn Ser Met Asp Pro Gly Ser Thr Pro Pro
 50                  55                  60

Ser Cys Cys Val Pro Thr Lys Leu Thr Pro Ile Ser Ile Leu Tyr Ile
 65                  70                  75                  80

Asp Ala Gly Asn Asn Val Val Tyr Lys Gln Tyr Glu Asp Met Val Val
                 85                  90                  95

Glu Ser Cys Gly Cys Arg
                100

<210> SEQ ID NO 14
<211> LENGTH: 102
<212> TYPE: PRT
<213> ORGANISM: Bos taurus

<400> SEQUENCE: 14

Cys Ser Lys Lys Pro Leu His Val Asn Phe Lys Glu Leu Gly Trp Asp
 1               5                  10                  15

Asp Trp Ile Ile Ala Pro Leu Glu Tyr Glu Ala Phe His Cys Glu Gly
                 20                  25                  30

Val Cys Asp Phe Pro Leu Arg Ser His Leu Glu Pro Thr Asn His Ala
             35                  40                  45

Ile Ile Gln Thr Leu Met Asn Ser Met Asp Pro Gly Ser Thr Pro Pro
 50                  55                  60

Ser Cys Cys Val Pro Thr Lys Leu Thr Pro Ile Ser Ile Leu Tyr Ile
 65                  70                  75                  80

Asp Ala Gly Asn Asn Val Val Tyr Asn Glu Tyr Glu Glu Met Val Val
                 85                  90                  95

Glu Ser Cys Gly Cys Arg
                100

<210> SEQ ID NO 15
<211> LENGTH: 102
<212> TYPE: PRT
<213> ORGANISM: Mus musculus

<400> SEQUENCE: 15
```

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 16
<211> LENGTH: 102
<212> TYPE: PRT
<213> ORGANISM: Artificial Sequence
<220> FEATURE:
<223> OTHER INFORMATION: danio mutant

<400> SEQUENCE: 16

Cys Ser Lys Lys Pro Leu His Val Asn Phe Arg Glu Leu Gly Trp Asp
1               5                   10                  15

Asp Trp Val Ile Ala Pro Leu Asp Tyr Glu Ala Tyr His Cys Glu Gly
            20                  25                  30

Met Cys Asp Phe Pro Leu Arg Ser His Leu Glu Pro Thr Asn His Ala
        35                  40                  45

Ile Ile Gln Thr Leu Met Asn Ser Met Asn Pro Ser Asn Met Pro Pro
    50                  55                  60

Ser Cys Cys Val Pro Ser Lys Leu Ser Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 17
<211> LENGTH: 102
<212> TYPE: PRT
<213> ORGANISM: Danio rerio

<400> SEQUENCE: 17

Cys Ser Lys Lys Ala Leu His Val Asn Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Asn Ser Thr Pro Pro
    50                  55                  60

Ser Cys Cys Val Pro Thr Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

```
Glu Gln Cys Gly Cys Arg
        100

<210> SEQ ID NO 18
<211> LENGTH: 102
<212> TYPE: PRT
<213> ORGANISM: Xenopus laevis

<400> SEQUENCE: 18

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala His His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asn Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
        100

<210> SEQ ID NO 19
<211> LENGTH: 102
<212> TYPE: PRT
<213> ORGANISM: Homo sapiens

<400> SEQUENCE: 19

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
        100

<210> SEQ ID NO 20
<211> LENGTH: 102
<212> TYPE: PRT
<213> ORGANISM: Cercopithecus aethiops

<400> SEQUENCE: 20

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
```

```
                    50                  55                  60
Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
            100

<210> SEQ ID NO 21
<211> LENGTH: 102
<212> TYPE: PRT
<213> ORGANISM: Macaca fascicularis

<400> SEQUENCE: 21

Cys Ser Arg Lys Pro Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
                20                  25                  30

Val Cys Asp Phe Pro Leu Arg Ser His Leu Glu Pro Thr Asn His Ala
             35                  40                  45

Ile Ile Gln Thr Leu Leu Asn Ser Met Ala Pro Asp Ala Ala Pro Ala
         50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
            100

<210> SEQ ID NO 22
<211> LENGTH: 102
<212> TYPE: PRT
<213> ORGANISM: Mus musculus

<400> SEQUENCE: 22

Cys Ser Arg Lys Ser Leu His Val Asp Phe Lys Glu Leu Gly Trp Asp
 1               5                  10                  15

Asp Trp Ile Ile Ala Pro Leu Asp Tyr Glu Ala Tyr His Cys Glu Gly
                20                  25                  30

Val Cys Asp Phe Pro Leu Arg Ser His Leu Glu Pro Thr Asn His Ala
             35                  40                  45

Ile Ile Gln Thr Leu Leu Asn Ser Met Ala Pro Asp Ala Ala Pro Ala
         50                  55                  60

Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
            100

<210> SEQ ID NO 23
<211> LENGTH: 102
<212> TYPE: PRT
<213> ORGANISM: Gallus gallus

<400> SEQUENCE: 23

Cys Ser Arg Lys Pro Leu His Val Asn Phe Lys Glu Leu Gly Trp Asp
 1               5                  10                  15
```

```
Asp Trp Ile Ile Ala Pro Leu Asp Tyr Glu Ala Tyr His Cys Glu Gly
            20                  25                  30

Val Cys Asp Phe Pro Leu Arg Ser His Leu Glu Pro Thr Asn His Ala
            35                  40                  45

Ile Ile Gln Thr Leu Met Asn Ser Met Asp Pro Glu Ser Thr Pro Pro
        50                  55                  60

Ser Cys Cys Val Pro Ser Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

Glu Thr Cys Gly Cys Arg
                100

<210> SEQ ID NO 24
<211> LENGTH: 102
<212> TYPE: PRT
<213> ORGANISM: Danio rerio

<400> SEQUENCE: 24

Cys Ser Arg Lys Pro Leu His Val Asn Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
            35                  40                  45

Ile Ile Gln Thr Leu Met Asn Ser Met Asp Pro Glu Ser Thr Pro Pro
        50                  55                  60

Ser Cys Cys Val Pro Ser Lys Leu Ser Pro Ile Ser Ile Leu Tyr Ile
65                  70                  75                  80

Asp Ser Gly Asn Asn Val Val Tyr Lys Gln Tyr Glu Asp Met Val Val
                85                  90                  95

Glu Ser Cys Gly Cys Arg
                100
```

HIGH ACTIVITY GROWTH FACTOR MUTANTS

CROSS REFERENCE TO RELATED APPLICATIONS

This application is a continuation of U.S. Ser. No. 13/457,957, filed Apr. 27, 2012, which is a divisional of U.S. Ser. No. 12/094,227 filed May 19, 2008, which issued on May 29, 2012, as U.S. Pat. No. 8,188,226; which is a 35 U.S.C. 371 National Phase Entry Application from PCT/EP2006/011074, filed Nov. 17, 2006, which claims the benefit of European Patent Application No. 05025261.8 filed on Nov. 18, 2005, the disclosures of which are incorporated herein in their entirety by reference.

The invention relates to novel recombinant biosynthetic growth factor mutants exhibiting improved biological activity. Said improved protein activity is achieved by the substitution of specific amino acids of the original growth factor proteins which are naturally occurring proteins of the transforming growth factor-beta superfamily of signalling molecules. The recombinant proteins provided herein are particularly suitable for inducing regeneration, growth stimulation and -differentiation of various cells, tissues and organs. The invention also relates to nucleic acid molecules coding for said recombinant protein mutants, expression vectors and host cells containing the nucleic acid molecules, antibodies directed against said protein mutants, pharmaceutical compositions and methods for producing the growth factor mutants.

The transforming growth factor-beta (TGF-beta) superfamily of proteins comprises more than 35 members including TGF-betas, bone morphogenetic proteins (BMPs), activins, inhibins and growth/differentiation factors (GDFs). TGF-beta superfamily proteins promote cell proliferation and -differentiation as well as tissue formation and are relevant for a wide range of medical treatment methods and applications. These dimeric molecules act through specific receptor complexes that are composed of type I and type II serine/threonine receptor kinases. The receptor kinases subsequently activate Smad proteins, which then propagate the signals into the nucleus to regulate target gene expression. Smad independent signalling pathways are also initiated by these receptors and result in induction of the MAP Kinase pathway. Smads are a unique family of signal transduction molecules that can transmit signals directly from the cell surface receptors to the nucleus, where they regulate transcription by interacting with DNA binding partners as well as transcriptional coactivators and corepressors.

The members of this protein family are initially synthesized as large precursor proteins which subsequently undergo proteolytic cleavage at a cluster of basic residues approximately 110-140 amino acids from the C-terminus, thus releasing the C-terminal mature protein part from the N-terminal prodomain. All mature polypeptides are structurally related and contain a conserved bioactive domain comprising six or seven canonical cysteine residues which are responsible for the characteristical three-dimensional "cystine-knot" motif of these proteins.

The various superfamily members can be further classified into distinct subfamilies and -groups, based on the extent of the homology/identity of their cystine-knot motif. The overlapping families of bone morphogenetic proteins and growth/differentiation factors (GDFs) are known to play a diverse set of roles in the skeletal system and other tissues (see i.e. Ducy and Karsenty 2000, Kidney Int. 57, 2207-2214 for a review). Especially human GDF-5 (the protein is also known as MP52, CDMP-1 or sometimes as BMP-14), GDF-6 (CDMP-2, BMP13) and GDF-7 (CDMP-3, BMP-12) have been grouped together by several authors due to their comparable biological properties and the extraordinarily high degree of amino acid sequence identity (see i.e. Mikic 2004, Annals of Biomedical Engineering 32, 466-476; Wolfman et al. 1997, J. Clin. Invest. 100, 321-330).

Besides the prominent functions of the GDF-5/-6/-7 subgroup in the de novo formation of bone and cartilage (Cheng et al. 2003, J. Bone & Joint Surg. Am. 85-A, 1544-1552; Settle et al. 2003, Developm. Biol. 254, 116-130), it has repeatedly been demonstrated that the members of this subgroup are also important inducers and regulators of tendon and ligament (Wolfman et al. 1997, J. Clin. Invest. 100, 321-330), nerve tissues (Farkas et al. 1997, Neurosci Lett. 236, 120-122; Watakabe et al. 2001, J. Neurochem. 76, 1455-1464), periodontal ligament and teeth (Sena et al 2003, J. Dent. Res. 82, 166-171; Morotome et al. 1998, Biochem. Biophys. Res. Commun. 244, 85-90), and other tissues.

The gene and protein structures of various naturally occurring BMPs/GDFs including GDF-5, GDF-6 and GDF-7 have previously been elucidated. Several loss-of-function mutants of GDF-5 could be identified which i.e. lead to shortening of fingers and toes (brachydactyly type C) and other skeletal abnormalities such as brachypodism in animals (Storm et al. 1994, Nature 368, 639-643) and acromesomelic displasias in man (Thomas et al. 1996, Nature Gen. 12, 315-317). Regarding these mutants it has been found that specific amino acid substitutions at positions 173, 204, 400, 438, 441 and 498 of human GDF-5 either reduce or completely abolish the protein function (Schwabe et al. 2004, Amer. J. Med Genet. 124A, 356-363). In contrast, only very few GDF-mutants with enhanced biological activity are known to date. A rare example is disclosed in WO01/11041 and relates to active monomeric GDF-5 which lacks the cysteine residue normally responsible for dimerization.

The search for the molecules responsible for bone-, cartilage-, and other tissue-inductive activity has led to the discovery of a set of molecules called growth/differentiation factors. Due to their unique tissue inductive activities these proteins have been successfully applied in therapeutic research and regenerative surgery in which they promote and assist the natural healing process of damaged tissues, either alone or in combination with specific carrier and/or matrix materials. Nevertheless there is a great need to develop improved and more efficient forms of these proteins for such purposes.

This object is solved according to the invention by providing novel recombinant proteins derived from GDF-5-related proteins which exhibit improved biological activity as described herein and in the attached claims.

BRIEF DESCRIPTION OF THE DRAWINGS

FIG. 1, shows additional features of the human GDF-5 precursor protein according to SEQ ID NO: 1.

FIG. 2 shows a comparison of the 102 aa cystine-knot-domains of human GDF-5 (SEQ ID NO: 1; the 400-501 amino acid fragment), human GDF-6 (sequence 2 from U.S. Pat. No. 5,658,882; SEQ ID NO: 6) and human GDF-7 (sequence 26 from U.S. Pat. No. 5,658,882; SEQ ID NO: 7). Amino acid residues which are identical in all three molecules are highlighted in black. Residues M453 and M456 of human GDF-5 and equivalent residues of human GDF-6 and GDF-7 are marked by arrows.

FIG. 4 lists the sequence identities of cystine-knot-domains of known BMPs and GDFs to the cystine-knot-domain of human GDF-5.

DETAILED DESCRIPTION OF THE INVENTION

In order to avoid misunderstandings and ambiguities, some frequently used terms herein are defined and exemplified as follows:

The term "cystine-knot-domain" as used herein means the well known and conserved cysteine-rich amino acid region which is present in the mature parts of TGF-beta superfamily proteins such as human GDF-5 and which forms a three-dimensional protein structure known as cystine-knot. In this domain, the respective location of the cysteine residues to each other is important and is only allowed to vary slightly in order not to lose the biological activity. Consensus sequences for cystine-knot domains are known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 precursor protein (SEQ ID NO: 1) comprises the amino acids 400-501 (see also FIG. 1).

The term "GDF-5-related protein" as used herein means any naturally occurring or artificially created protein which comprises a cystine-knot-domain with an amino acid identity of at least 60% to the 102 aa cystine-knot domain of human GDF-5 (amino acids 400-501 of FIG. 1/SEQ ID NO: 1) and which carries a methionine residue at a position equivalent to residue methionine 453 (M453) of human GDF-5, and a methionine or leucine residue at a position equivalent to methionine 456 (M456) of human GDF-5. Included are proteins belonging to the group of GDF-5, GDF-6 and GDF-7 proteins from vertebrate or mammalian species as well as recombinant variants thereof as long as these proteins fulfill the above mentioned requirements.

Figure 3:
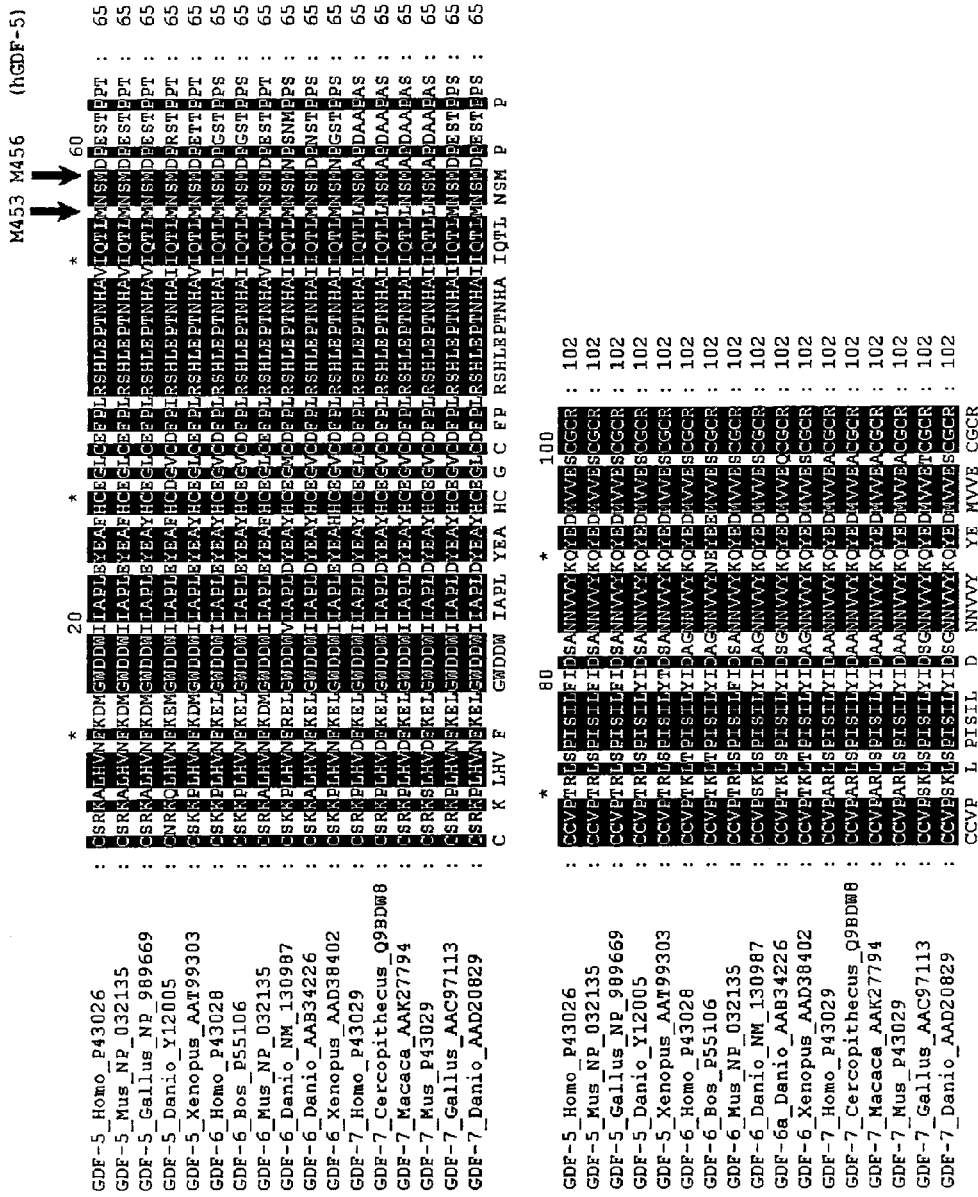
FIG. 3 shows a comparison of the 102 aa cystine-knot-domains of vertebrate GDF-5, -6 and -7 sequences from the genus *Homo*, further *Cercopithecus, Macaca, Bos, Mus, Gallus Danio* and *Xenopus*, which are available in the "Entrez" NCBI protein database (www.ncbi.nlm.nih.gov/Entrez/) under the accession numbers is shown in the figure.

Non-limiting examples of GDF-5-related proteins according to the definition above are human GDF-5 (disclosed as MP52 in WO95/04819 and in Hötten et al. 1994, Biochem. Biophys Res. Commun. 204, 646-652), recombinant human GDF-5/MP52 (WO96/33215), mouse GDF-5 (U.S. Pat. No. 5,801,014), CDMP-1 (WO96/14335), HMW human MP52s (WO97/04095), rabbit GDF-5 (Sanyal et al. 2000, Mol Biotechnol. 16, 203-210), human GDF-6/BMP-13 (U.S. Pat. No. 5,658,882), bovine GDF-6 (NCBI accession no P55106), mouse GDF-6 (NCBI accession no NP_038554), GDF-6/CDMP-2 (WO96/14335), human GDF-7/BMP-12 (U.S. Pat. No. 5,658,882), mouse GDF-7 (NCBI accession no AAP97721), GDF-7/CDMP-3 (WO96/143335), chicken GDF-5 (NCBI accession no. NP_989669), *Xenopus laevis* GDF-5 (NCBI accession no. AAT99303), monomeric GDF-5, -6 and -7 (WO 01/11041 and WO99/61611), as shown in FIGS. 3 and 4.

The term "ML-mutant" as used herein means a recombinant protein derived from a GDF-5-related protein in which, after alignment with human GDF-5 as described in this application, the amino acid equivalent to methionine 453 (M453) of human GDF-5 is not methionine, and/or the amino acid equivalent to methionine 456 (M456) of human GDF-5 (SEQ ID NO: 1) is not methionine (M) or leucine (L).

The term "improved biological activity" as used herein relates to a biological activity of a ML-mutant amounting to at least 120% of the activity of the respective non-mutated protein.

The term "biological activity" denotes the activity of a GDF-5-related protein as measured by one or more of the following assays:

a) an in vitro alkaline phosphatase assay (ALP), e.g. as described in Takuwa et al. (1989), Am. J. Physiol. 257, E797-E803);

b) measurement of increased survival of dopaminergic neurons as described for example by Krieglstein et al. 1995 (J. Neuroscience Res. 42, 724-732) or Sullivan et al. 1997 (Neuroscience Letters 233, 73-76);

c) the outgrowth of nerve fibers from embryonic retina as measured e.g. as described i.e. in WO97/03188;

d) the angiogenic potential of these proteins as verified for example in an in vivo corneal micropocket model as described in Yamashita et al. 1997 (Exp. Cell Research 235, 218-226);

e) effects of GDF-5-related proteins on the terminal differentiation of myoblasts as determined as described e.g. by Inada et al 1996 (Biochem Biophys Res Commun. 222, 317-322);

f) in vivo tests measuring the inductive potential of such proteins concerning tendon and ligament e.g. as disclosed in Wolfman et al. 1997, J. Clin. Invest. 100, 321-330;

g) measurement of the signal transduction cascade through the activation of Smads using a reportergene assay based on the Smad-binding-elements preceding the firefly luciferase gene e.g. as previously described (Nohe et al., 2002. J Biol Chem. 277, 5330-5338.)

The term "variant" as used herein means any of the following polypeptides:

a) biologically active fragments of a protein b) protein constructs which contain additional sequences in excess to the original sequence of the protein c) any combination of a) and b)

The GDF-5/-6/-7 group of TGF-beta superfamily proteins, comprising GDF-5 as its best characterized member, is highly conserved among vertebrate/mammalian species (Ducy and Karsenty 2000, Kidney Int. 57, 2207-2214). It has now surprisingly been found by means of mutational studies and other experiments that amino acid residues which correspond to methionine 453 (M453) and methionine 456 (M456) of human GDF-5 can be substituted with some specified amino acids without negative effects on the protein function. Moreover, these substitutions even increase the biological activity of the proteins significantly.

This embodiment of the invention is further illustrated by the FIGS. 1, 2 and 3. FIG. 1 shows the human GDF-5 precursor protein (Hötten et al. 1994, Biochem. Biophys Res. Commun. 204, 646-652) which consists of a 381 aa prodomain (aa 1-381 including signal peptide (aa 1-27), bold letters) and a 120 aa mature part (aa 382-501). The mature part or especially the cystine-knot-domain (aa 400-501, underlined) are sufficient for the biological function of the protein. Residues M453 and M456 (grey boxes) are located within this cystine-knot domain. Corresponding residues in the cystine-knot-domains of other GDF-5-related proteins are shown in FIG. 2 and FIG. 3 (marked by arrows). Corresponding residues in proteins not shown in these figures can be easily determined by a sequence alignment with human GDF-5.

It has been found in GDF-5-related proteins that when the methionine residue at a position corresponding to methionine 453 (M453) of human wild-type GDF-5 (SEQ. ID NO 1) is replaced with an amino acid chosen from alanine (A), valine (V) or isoleucine (I), the resulting recombinant protein has increased biological activity.

In a preferred embodiment, the chosen amino acid is valine (V) for the position M453.

It has also been found that when the methionine residue at a position corresponding to methionine 456 (M456) of human wild-type GDF-5 (SEQ. ID NO 1) is replaced with an amino acid chosen from alanine (A), valine (V) or isoleucine (I), either independently, or in combination with a replacement of M453, the resulting recombinant protein has increased biological activity.

In a preferred embodiment, the chosen amino acid is valine (V) for the position M456.

These ML-mutants of GDF-5-related proteins in which the M453 and/or M456 equivalents are substituted with the amino acids specified above exhibit a biological activity greatly outperforming the activity of the respective nonmutated proteins.

Figure 5:
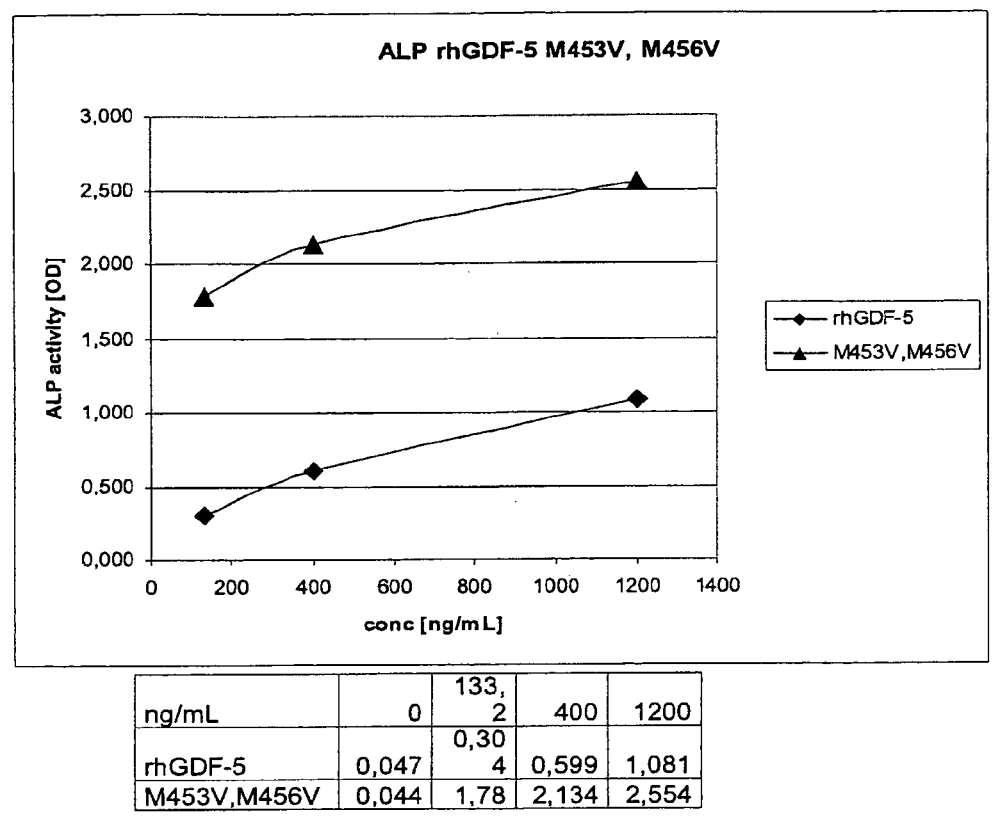
FIG. 5 shows the results of an alkaline phosphatase assay (ALP) with recombinant human GDF-5 (rh-GDF-5) and hGDF-5 ML-mutant M453V/M456V (as described in example 2).

As an example, FIG. 5 shows the enhanced ability of hGDF-5 ML-mutant M453V/M456V to induce alkaline phosphatase in vitro. The mutant protein exhibits a biological activity of 585.5% (at 133 ng/ml), 356.3% (at 400 ng/ml) and 236.3% (at 1200 ng/ml) of the activity of wildtype protein (rh-GDF-5) in this assay (average of multiple experiments). Thus, the average activity is 585.5+356.3+236.3:3=392.7% of the activity of wildtype protein (rh-GDF-5). The minimal activity measured for the mutant at a single protein concentration and in a single experiment was 150% of the activity of the wild-type protein.

Thus, encompassed by the invention are ML-mutants which exhibit an improved biological activity amounting to at least 120% of the activity of the respective non-mutated protein. Especially preferred are GDF-5-related ML-mutants with improved biological activities of at least 150%, preferably 160%, more preferably at least 170%, more preferably at least 180%, and most preferably at least 200% of the biological activity of the respective non-mutated protein.

The biological activities of GDF-5-related proteins and ML-mutants thereof i.e. in the field of induction of bone, cartilage and connective tissue such as i.e. periodontal ligament can be easily determined with the help of established test systems. Most useful and preferred is a common in vitro test known as alkaline phosphatase (ALP) assay (Takuwa et al. 1989, Am. J. Physiol. 257, E797-E803), which is also demonstrated in example 2/FIG. 5. GDF-5-related proteins have been demonstrated to increase alkaline phosphatase activity i.e. in ROB-C26 osteoprogenitor cells (Yamaguchi et al. 1991, Calcif. Tissue Int. 49, 221-225) as described in WO95/04819, in embryonic ATDC5 cells (Riken Gene Bank, ROB 0565), in mouse stromal MCHT-1/26 cells, and in periodontal ligament (HPDL) cells as shown in Nakamura et al. 2003, J. Periodontal Res. 38, 597-605.

The GDF-5-related proteins as defined herein comprise a cystine-knot-domain with an amino acid identity of at least 60%, preferably at least 75%, more preferably at least 80%, more preferably at least 90%, and most preferably at least 95%, to the 102 aa cystine-knot domain of human GDF-5. A limiting value of 60% is well suitable to separate members of the GDF-5/-6/-7 group of proteins as well as variants thereof from further proteins such as other GDFs and BMPs. A comparison of the 102 aa cystine-knot-domains of human GDF-5, human GDF-6 and human GDF-7 (FIG. 2) reveals the high grade of amino acid identity between these proteins. Human GDF-6 shares 87 (85%) and human GDF-7 83 (81%) identical residues with the cystine-knot-domain of human GDF-5. The respective domains of GDF-5/-6/-7 molecules from other vertebrate and mammalian species which have been identified so far also show very high identity percentages of at least 75% (between 79% and 99%), when compared with human GDF-5 (FIG. 4). In contrast, GDFs and BMPs not belonging to the GDF-5/-6/-7 subgroup display much lower identity values below 60%.

The determination of corresponding amino acid positions in related amino acid sequences as well as the calculation of percentages of identity between can be performed with the help of well known alignment algorithms and optionally computer programs using these algorithms. The amino acid identities in this patent application have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in:

Thompson, J. D., Gibson, T. J., Plewniak, F., Jeanmougin, F. and Higgins, D. G. (1997)

The ClustalX windows interface: flexible strategies for multiple sequence alignment aided by quality analysis tools. Nucleic Acids Research 24:4876-4882.

ClustalX is a windows interface for the ClustalW multiple sequence alignment program and is i.e. available from various sources, i.e. by anonymous ftp from gbmc.u-strasbq.fr, embl-heidelberq.de, ebi.ac.uk or via download from the following webpage: www-igbmc.u-strasbq.fr/BioInfo/. The ClustalW program and algorithm is also described in detail in:

Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research 22:4673-4680.

The ML-mutants according to the invention which are derived from GDF-5-related proteins are generally applicable in every indication in which GDF-5-related proteins such as GDF-5, GDF-6 and GDF-7 are also useful. It has been demonstrated that GDF-5-related proteins are important inducers and regulators/differentiators of i.e. bone and cartilage (Cheng et al. 2003, J. Bone & Joint Surg. Am. 85-A, 1544-1552; Settle et al. 2003, Developm. Biol. 254, 116-130), connective tissue such as tendon and ligament (Wolfman et al. 1997, J. Clin. Invest. 100, 321-330), nerve tissue (Farkas et al. 1997, Neurosci Lett. 236, 120-122; Watakabe et al. 2001, J. Neurochem. 76, 1455-1464), stem cells (Shimaoka et al. 2003, J. Biomed. Materials Res. Part A 68A, 168-176; Bai et al. 2004, Biochem. Biophys. Res. Commun. 325, 453-460) and/periodontal ligament and teeth (Sena et al 2003, J. Dent. Res. 82, 166-171; Morotome et al. 1998, Biochem. Biophys. Res. Commun. 244, 85-90).

In a preferred embodiment, the ML-mutant comprises a sequence which matches one of the following generic amino acid sequences a) [SEQ ID NO: 3]
$CX_1X_2KX_3LHVX_4FX_5X_6X_7GWDDWX_8IAPLX_9YEAX_{10}HCX_{11}GX_{12}$
$CX_{13}FPX_{14}RSHLEPTNHAX_{15}$
$IQTLZ_1NSMX_{16}PX_{17}X_{18}X_{19}PX_{20}X_{21}CCVPX_{22}X_{23}LX_{24}PISIL$
$X_{25}X_{26}DX_{27}X_{28}NNVVYX_{29}X_{30}YEX_{31}MVVEX_{32}CGCR$
or b) [SEQ ID NO: 4]
$CX_1X_2KX_3LHVX_4FX_5X_6X_7GWDDWX_8IAPLX_9YEAX_{10}HCX_{11}GX_{12}$
$CX_{13}FPX_{14}RSHLEPTNHAX_{15}$
$IQTLMNSZ_2X_{16}PX_{17}X_{18}X_{19}PX_{20}X_{21}CCVPX_{22}X_{23}LX_{24}PISIL$
$X_{25}X_{26}DX_{27}X_{28}NNVVYX_{29}X_{30}YEX_{31}MVVEX_{32}CGCR$
or c) [SEQ ID NO: 5]
$CX_1X_2KX_3LHVX_4FX_5X_6X_7GWDDWX_8IAPLX_9YEAX_{10}HCX_{11}GX_{12}$
$CX_{13}FPX_{14}RSHLEPTNHAX_{15}$
$IQTLZ_1NSZ_2X_{16}PX_{17}X_{18}X_{19}PX_{20}X_{21}CCVPX_{22}X_{23}LX_{24}PISIL$
$X_{25}X_{26}DX_{27}X_{28}NNVVYX_{29}X_{30}YEX_{31}MVVEX_{32}CGCR$, and wherein
every X denotes any amino acid,
$Z_1$ denotes alanine (A), isoleucine (I), or valine (V),
$Z_2$ denotes alanine (A), isoleucine (I), or valine (V).

In a more preferred embodiment, the ML-mutant comprises a sequence which matches one of the above mention generic amino acid sequences and wherein
$X_1$ denotes asparagine (N) or serine (S)
$X_2$ denotes arginine (R) or lysine (K)
$X_3$ denotes alanine (A), glutamine (Q), proline (P) or serine (S)
$X_4$ denotes asparagine (N) or aspartic acid (D)
$X_5$ denotes arginine (R) or lysine (K)
$X_6$ denotes aspartic acid (D) or glutamic acid (E)
$X_7$ denotes leucine (L) or methionine (M)
$X_8$ denotes isoleucine (I) or valine (V)
$X_9$ denotes aspartic acid (D) or glutamic acid (E)
$X_{10}$ denotes histidine (H), phenylalanine (F) or tyrosine (Y)
$X_{11}$ denotes aspartic acid (D) or glutamic acid (E)
$X_{12}$ denotes leucine (L), methionine (M) or valine (V)
$X_{13}$ denotes aspartic acid (D) or glutamic acid (E)
$X_{14}$ denotes isoleucine (I) or leucine (L)
$X_{15}$ denotes isoleucine (I) or valine (V)
$X_{16}$ denotes alanine (A), asparagine (N) or aspartic acid (D)
$X_{17}$ denotes arginine (R), asparagine (N), aspartic acid (D), glutamic acid (E), glycine (G) or serine (S)
$X_{18}$ denotes alanine (A), asparagine (N), serine (S) or threonine (T)
$X_{19}$ denotes alanine (A), methionine (M) or threonine (T)
$X_{20}$ denotes alanine (A) or proline (P)
$X_{21}$ denotes serine (S) or threonine (T)
$X_{22}$ denotes alanine (A), serine (S) or threonine (T)
$X_{23}$ denotes arginine (R) or lysine (K)
$X_{24}$ denotes serine (S) or threonine (T)
$X_{25}$ denotes phenylalanine (F) or tyrosine (Y)
$X_{26}$ denotes isoleucine (I) or threonine (T)
$X_{27}$ denotes alanine (A) or serine (S)
$X_{28}$ denotes alanine (A) or glycine (G)
$X_{29}$ denotes asparagine (N) or lysine (K)
$X_{30}$ denotes glutamic acid (E) or glutamine (Q)
$X_{31}$ denotes aspartic acid (D) or glutamic acid (E),
$X_{32}$ denotes alanine (A), glutamine (Q), serine (S) or threonine (T)
$Z_1$ denotes alanine (A), isoleucine (I), or valine (V),
$Z_2$ denotes alanine (A), isoleucine (I), or valine (V).

These generic sequences have been compiled from a comparison of the cystine-knot domains of vertebrate GDF-5, GDF-6 and GDF-7 sequences according to FIG. 3. Positions which are not conserved in the aligned proteins are denoted with an X in the generic sequences. Positions which are mutated according to the present invention are denoted with a Z.

In another preferred embodiment, the ML-mutant protein according to the invention is an ML-mutant of a vertebrate or recombinant GDF-5 protein or a variant thereof. Most preferred are ML-mutants of a mammalian GDF-5 protein or variants thereof. Examples for vertebrate and mammalian GDF-5 proteins are: human GDF-5 (disclosed as MP52 in WO95/04819 and as human GDF-5 in Hötten et al. 1994, Biochem. Biophys Res. Commun. 204, 646-652), recombinant human GDF-5/MP52 (WO96/33215), HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol Biotechnol. 16, 203-210), chicken (*Gallus gallus*) GDF-5 (NCBI accession no. NP_989669), african clawed frog (*Xenopus laevis*) GDF-5 (NCBI accession no. AAT99303).

Another preferred embodiment of the invention includes ML-mutant proteins of monomeric GDF-5-related proteins. In these monomeric proteins, the cysteine which is responsible for dimer formation is either substituted by another amino acid or deleted. Such proteins are e.g. described in WO 01/11041 and WO 99/61611, which are herewith incorporated by reference. An especially preferred monomeric protein is recombinant monomeric GDF-5 as disclosed therein.

Enclosed in these embodiments are also ML-mutants of allelic versions of the aforementioned genes/proteins as well as ML-mutants of the vertebrate, mammalian and recombinant proteins or variants thereof having additional mutations such as substitutions, additions and deletions, as long as these additional mutations have no essential effect on protein activity.

In general, the ML-mutant of the vertebrate or mammalian or recombinant GDF-5 protein or variant thereof is expected to show all already described activities of GDF-5 and can be applied wherever the above mentioned recombinant and wild-type GDF-5 forms are been successfully used. For example, GDF-5 is considered to be a very effective promoter of bone and cartilage formation as well as connective tissue formation (see for example WO 95/04819, Hötten et al. 1996, Growth Factors 13, 65-74; Storm et al. 1994, Nature 368, 639-643; Chang et al. 1994, J. Biol. Chem. 269, 28227-28234) and formation of connective tissue attachment (EP 0 831 884. In this context, GDF-5 is useful for applications concerning the joints between skeletal elements (see for example Storm & Kingsley 1996, Development 122, 3969-3979). One example for connective tissue is tendon and ligament (Wolfman et al. 1997, J. Clin. Invest. 100, 321-330; Aspenberg & Forslund 1999, Acta Orthop Scand 70, 51-54; WO 95/16035). The protein is helpful for meniscus and spinal/intervertebral disk repair (Walsh et al. 2004, Spine 29, 156-63) and spinal fusion applications (Spiro et al. 2000, Biochem Soc Trans. 28, 362-368). GDF-5 can be beneficially applied in tooth (dental and periodontal) applications (see for example WO 95/04819; WO 93/16099; Morotome et al. 1998, Biochem Biophys Res Comm 244, 85-90) such as the regeneration of dentin or periodontal ligament.

GDF-5 is also useful in wound repair of any kind. It is also beneficial for promoting tissue growth in the neuronal system and survival of e.g. dopaminergic neurons. In this context, GDF-5 can be used for treating neurodegenerative disorders like e.g. Parkinson's disease and possibly also Alzheimer's disease or Huntington chorea tissues (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). GDF-5 allows to maintain nervous function or to retain nervous function in already damaged tissues. GDF-5 is therefore considered to be a generally applicable neurotrophic factor.

It is also useful for diseases of the eye, in particular retina, cornea and optic nerve (see for example WO 97/03188; You et al. (1999), Invest Opthalmol Vis Sci 40, 296-311), for hair growth and the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

On the one hand, there is the prevention or therapy of diseases associated with bone and/or cartilage damage or affecting bone and/or cartilage disease, or generally situations, in which cartilage and/or bone formation is desirable or for spinal fusion, and on the other hand, there is prevention or therapy of damaged or diseased tissue associated with connective tissue including tendon and/or ligament, periodontal or dental tissue including dental implants, neural tissue including CNS tissue and neuropathological situations, tissue of the sensory system, liver, pancreas, cardiac, blood vessel, renal, uterine and thyroid tissue, skin, mucous membranes, endothelium, epithelium, for promotion or induction of nerve growth, tissue regeneration, angiogenesis, wound healing including ulcers, burns, injuries or skin grafts, induction of proliferation of progenitor cells or bone marrow cells, for maintenance of a state of proliferation or differentiation for treatment or preservation of tissue or cells for organ or tissue transplantation, for integrity of gastrointestinal lining, for treatment of disturbances in fertility, contraception or pregnancy.

Diseases concerning sensory organs like the eye are also to be included in the preferred indication of the pharmaceutical composition according to the invention. As neuronal diseases again Parkinson's and Alzheimer's diseases can be mentioned as examples.

Figure 6:
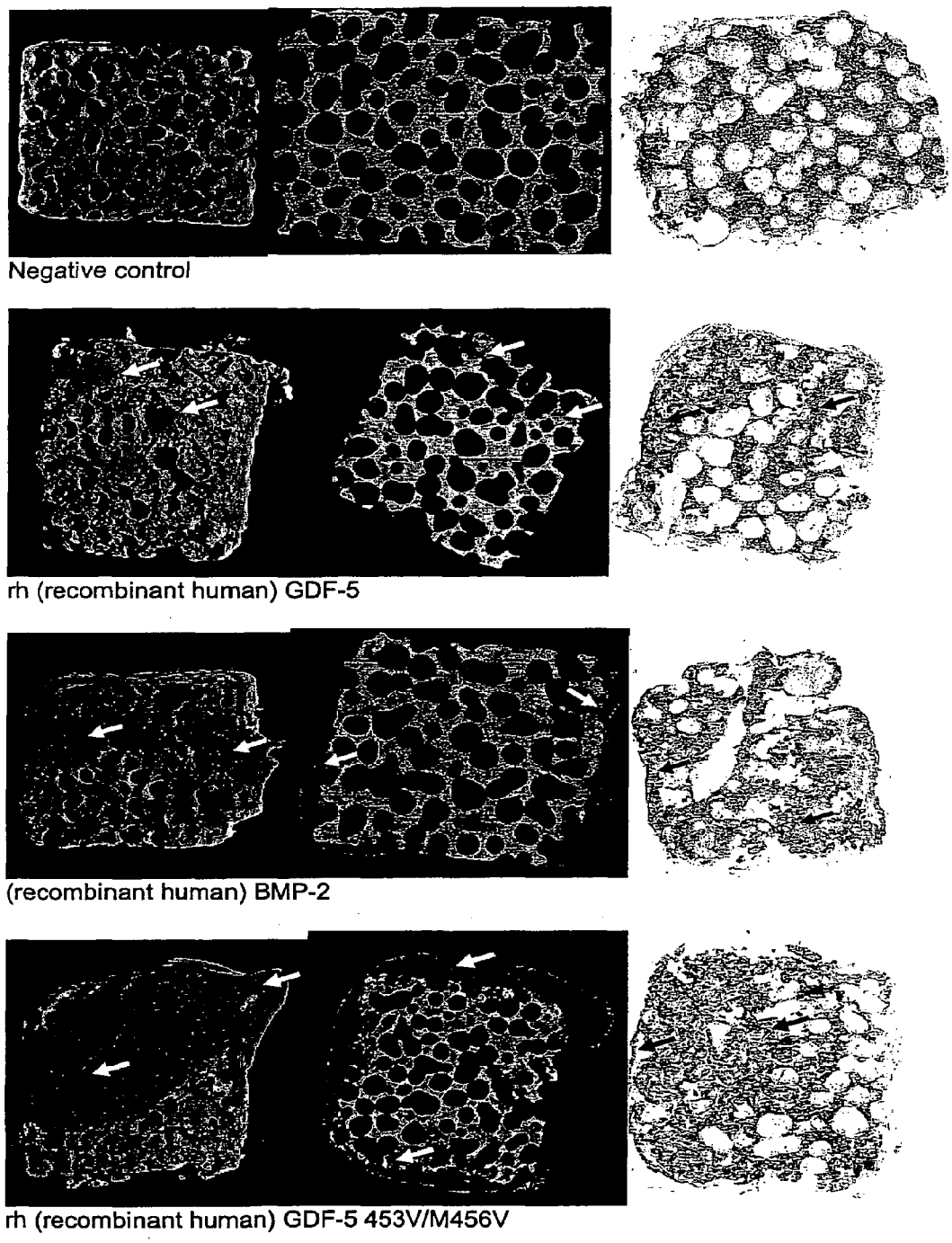
FIG. 6 shows histological cross-sections (AlizarinRed-S staining of newly formed calcium) and µCT scans of growth factor-treated scaffolds 4 weeks after implantation in SCID mice according to example 3.

Example 3 and FIG. 6 describe the results of an alkaline phosphatase assay with recombinant human GDF-5 (WO96/33215) and the ML-mutant M453V/M456V of recombinant human GDF-5 (rhGDF-5). Recombinant human GDF-5 was used as a standard/control with 100% biological activity.

The mutant protein exhibits a biological activity of 585.5% (at 133 ng/ml), 356.3% (at 400 ng/ml) and 236.3% (at 1200 ng/ml) of the activity of wildtype protein (rh-GDF-5) in this assay (average of multiple experiments). Thus, the average activity is 585.5+356.3+236.3:3=392.7% of the activity of wildtype protein (rh-GDF-5). The minimal activity measured for the mutant at a single protein concentration and in a single experiment was 150% of the activity of the wild-type protein.

The ML-mutants according to the invention can be easily produced in various prokaryotic and eukaryotic expression systems, in particular by expression in prokaryotes and subsequent renaturation/refolding according to known methods (see i.e. WO96/33215).

A further subject matter of the present invention is a nucleic acid encoding an ML-mutant according to the invention. The nucleic acid has a sequence such that a substitution of one or both residues equivalent to M453 and M456 of human GDF-5 with one of the amino acids specified in this application is achieved. The base triplets coding for these amino acids and the degeneracy of the genetic code are generally known. The nucleic acid can be a DNA sequence and/or a RNA sequence, as long as the protein according to the invention can be obtained from this nucleic acid upon expression in a suitable system.

Expression vectors are a further subject matter of the present invention, wherein the nucleic acid is inserted in a suitable vector system, the vector system being selected according to the desired expression of the protein. The vector system can be a eukaryotic vector system, but preferred is a prokaryotic vector system, with which the proteins can be produced in a particularly easy and pure manner. A suitable expression vector is i.e. shown in WO96/33215. The expression vector can also be a viral vector which can be used i.e. in gene therapy approaches.

Host cells are also a subject matter of the present invention. The host cells are characterized in that they contain a nucleic acid or an expression vector according to the invention and that they are able to use the information present in the nucleic acids and in the expression vector, respectively, for the expression of ML-mutants according to the invention. Suitable host cells are preferably prokaryotic cells, in particular most *E. coli* strains. Particularly useful host strains are descendents of *E. coli* W3110 as shown e.g. in WO96/33215. In a preferred embodiment, host cells, preferably of human origin, may also be useful for transplantation to patients in need thereof.

Another subject matter of the present invention are antibodies against ML-mutants. These antibodies according to the present invention are specific for the claimed recombinant ML-mutant. Preferably, they are specific for the cystine knot regions of GDF-5-related proteins containing one or more of the amino acid replacements described herein. Preferably, the antibodies are specific for a region of a recombinant protein derived from a GDF-related protein according to the invention spanning amino acid 400-495, preferably 420-460, more preferably 440-460, more preferably amino acids 453-456. These antibodies according to the present invention can be generated by using those fragments of the protein of the invention as described above as immunogens to generate antibodies by known methods. The antibodies can be monoclonal or polyclonal and they can be of any isotype. Also comprised are antibody fragments such as Fab-fragments or $Fab_2$-fragments. The antibodies can also be humanized antibodies or chimeric antibodies etc.

Further subject matters of the present application are pharmaceutical and/or diagnostic compositions comprising at least one ML-mutant of a GDF-5-related protein or a nucleic acid or a vector or host cell according to the invention. Suitable are generally all pharmaceutical composition which have already been published in context with GDF-5-related proteins. An expression vector or a host cell can be considered to be advantageous as active substances in a pharmaceutical and/or diagnostic composition. Also combinations of a protein according to the invention with other proteins can be used in preferred pharmaceutical compositions. Especially preferred for neuronal applications are combinations with other TGF-beta superfamily proteins such as i.e. GDNF (see WO 97/03188). For applications concerning cartilage and/or bone the combination with BMPs in general or with a cartilage maintenance-inducing protein such as BMP-9 (see e.g. WO 96/39170) is useful. Combinations with other proteins such as i.e. NGF, BDNF, EGF, PDGF, NT-3, -4, -5, chordin and/or hedgehog proteins are also possible (see i.e. WO97/03188). Of course this invention also comprises pharmaceutical compositions containing further substances like e.g. pharmacologically acceptable auxiliary and carrier substances. The formulation may include antioxidants, preservatives, colouring, flavouring and emulsifying agents, suspending agents, solvents, fillers, bulking agents, buffers, delivery vehicles, excipients and/or pharmaceutical adjuvants. For example, a suitable carrier or vehicle may be water for injection, physiological saline solution, or a saline solution mixed with a suitable carrier protein such as serum albumin. A preferred antioxidant for the preparation of the composition of the present invention is ascorbic acid.

Cosmetic compositions known in the art, preferably hypoallergic and pH controlled are especially preferred, and include toilet waters, packs, lotions, skin milks or milky lotions. Said preparations contain, besides the active compound, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

The solvent or diluent of the pharmaceutical composition may be either aqueous or non-aqueous and may contain other pharmaceutically acceptable excipients which are capable of modifying and/or maintaining a pH, osmolarity, viscosity, clarity, scale, sterility, stability, rate of dissolution or odour of the formulation. Similarly other components may be included in the pharmaceutical composition according to the present invention in order to modify and/or maintain the rate of release of the pharmaceutically effective substance. Such modifying components are substances usually employed in the art in order to formulate dosages for parenteral administration in either unit or multi-dose form. The finally formulated pharmaceutical and/or diagnostic composition prepared according to the present invention may be stored in sterile vials in form of a solution, suspension, gel, emulsion, solid or dehydrated or lyophilized powder. These formulations may be stored either in a ready-to-use form or in a form, e.g. in case of a lyophilized powder, which requires reconstitution prior to administration. The above and further suitable pharmaceutical formulations are known in the art and are described in, for example, Gus Remington's Pharmaceutical Sciences (18th Ed., Mack Publishing Co., Eastern, Pa., 1990, 1435-1712). Such formulations may influence the physical state, stability, rate of in vivo release and rate of in vivo clearance of the pharmaceutically effective component. Other effective administration forms comprise parenteral slow-release, i.e. retarded, formulations, inhalent mists, or orally active formulations. For example, a slow-release formulation may comprise proteins bound to or incorporated into particulate preparations of polymeric compounds (such as polylactic acid, polyglycolic acid, etc.) or liposomes. The pharmaceutical composition according to the present invention may also be formulated for parenteral administration, e.g., by infusion or injection, and may also include slow-release or sustained circulation formulations. Such parenterally administered therapeutic compositions are typically in the form of pyrogen-free, parenterally acceptable aqueous solutions comprising the pharmaceutically effective component(s) in a pharmaceutically acceptable carrier and/or diluent.

The pharmaceutical composition may comprise a matrix material, i.e. in cases where regeneration of bone or cartilage is intended. It is advantageous to the protein, the nucleic acid, the expression vector or the host cell when they are applied in and/or on a biocompatible matrix material. Matrix material as used herein means a carrier or matrix acting as a scaffold for cell recruitment, attachment, proliferation and differentiation and/or as a potential delivery and storage device for ML-mutants of GDF-5-related proteins. In contrast to the solid matrices, carriers consist of amorphous materials having no defined surfaces and lacking a specific shape, i.e. alkylcelluloses, pluronics, gelatins, polyethylene glycols, dextrins, vegetable oils, sugars and other liquid and viscous substances.

Uses of GDF-5-related proteins or similar morphogens such as BMPs in combination with matrix materials are extensively published and described, such as for example in WO98/21972. These matrix materials are equally suitable for ML-mutants according to the invention. The matrix material can be transplanted into the patient, e.g. surgically, wherein the protein or the DNA encoding the protein can be slowly released from the matrix material and then be effective over a long period of time. All types of matrix materials are useful in accordance with the present invention, as long as they are biocompatible and selected for the intended area or indication of use. The matrix material can be a natural material, a modified natural material as well as a synthetic material. All already known matrices for morphogenetic proteins are encompassed. Examples of natural materials are e.g. autologous, heterologous or xenologous bone materials, collagen, e.g. collagen type I and III, or metals like titanium. Also other components of the extracellular matrix can be used. The extracellular matrix comprises for example the various collagens, as for example types I, II, V, IX, X, XI and XIII, further proteoglycanes and glycosaminoglycanes, as for example chondroitinsulfate, biglycane, decorine and/or hyaluronic acid, or noncollagenous proteins as for example osteopontin, laminin, fibronectin, vitronectin, thrombospondin, cartilage matrix protein and dentin phosphoprotein. All mentioned natural materials may also be used in artificially modified forms. Examples of modified natural materials are demineralized bone, thermoashed bone mineral, sintered bone or chemically crosslinked hyaluronic acid (hydrogel), or metal alloys. Examples of synthetic materials are polymers like polyglycolic acid, polylactide and polylactide derivatives such as e.g. polylactic acid, poly(lactide-co-glycolide), polylactid acid-polyethylene glycol or glycolide L-lactide copolymers, further polyphosphates, polyethylene glycol, polyoxyethylene polyoxypropylene copolymers or materials containing calcium phosphates such as beta-tricalcium phosphate ($Ca_3(PO_4)_2$), alpha-tricalcium phosphate and hydroxyl apatite. Further examples of other useful matrix materials belonging to one of the above mentioned groups are $Ca(OH)_2$, coral, natural bone mineral, chitin, non-demineralized bone particles, ceramic bone particles, ceramic dentin, irradiated cancellous bone chips, plaster of Paris, bioactive glass, apatite-wollastonite-containing glass ceramic. Also a combination of the above mentioned carriers and/or matrices can form the matrix material as for example the combination of hydroxy apatite and collagen (e.g. Healos, previously available from Orquest, Inc., CA, USA, [now DePuy Acromed, MA, USA]), a combination of polyglycolic acid and polylactic acid or polylactid derivatives, or coral-collagen composites. For a non limiting list of useful carriers and matrices see further i.e. Kirker-Head 2000, Advanced Drug Delivery 43, 65-92.

The following non-limiting examples together with the figures and sequence protocols are intended to further illustrate the invention.

SEQ ID NO: 1 and SEQ ID NO: 2 show the protein and DNA sequences, respectively, of the human GDF-5 precursor. In the preferred human GDF-5 protein mutants with improved biological activity, the methionine residue at position 453 and/or the methionine residue at position 456 are substituted with other amino acids.

As shown in FIG. 1, additional features of the human GDF-5 precursor protein according to SEQ ID NO: 1:

aa 001-381 pre-prodomain (bold letters)

aa 382-501 mature protein part aa 400-501 cystine-knot-domain (underlined)

aa 453 resisude methionine 453 (grey box)

aa 456 resisude methionine 456 (grey box)

A comparison of the 102 aa cystine-knot-domains of human GDF-5 (SEQ ID NO 1), human GDF-6 (sequence 2 from U.S. Pat. No. 5,658,882) and human GDF-7 (sequence 26 from U.S. Pat. No. 5,658,882) is made in FIG. 2. Amino acid residues which are identical in all three molecules are highlighted in black. Residues M453 and M456 of human GDF-5 and equivalent residues of human GDF-6 and GDF-7 are marked by arrows.

FIG. 3 shows a comparison of the 102 aa cystine-knot-domains of vertebrate GDF-5, -6 and -7 sequences from the genus *Homo*, further *Cercopithecus, Macaca, Bos, Mus, Gallus* Danio and *Xenopus*, which are available in the "Entrez" NCBI protein database (www.ncbi.nlm.nih.gov/Entrez/) under the accession numbers shown in the figure. Residues M453 and M456 of human GDF-5 and equivalent residues of the other proteins are marked by arrows.

| Sequence Name | SEQ ID NO: |
|---|---|
| GDF-5_Homo_P43026 | 8 |
| GDF-5_Mus_NP_032135 | 9 |
| GDF-5_Gallus_NP_989669 | 10 |
| GDF-5_Danio_Y12005 | 11 |
| GDF-5_Xenopus_AAT99303 | 12 |
| GDF-6_Homo_P43028 | 13 |
| GDF-6_Bos_P55106 | 14 |
| GDF-6_Mus_NP_032135 | 15 |
| GDF-6_Danio_NM_130987 | 16 |
| GDF-6_Danio_AAB34226 | 17 |
| GDF-6_Xenopus_AAD38402 | 18 |
| GDF-7_Homo_P43029 | 19 |
| GDF-7_Cercopithecus_Q9BDW8 | 20 |
| GDF-7_Macaca_AAK27794 | 21 |
| GDF-7_Mus_P43029 | 22 |
| GDF-7_Gallus_AAC97113 | 23 |
| GDF-7_Danio_AAD20829 | 24 |

The sequence identities of cystine-knot-domains of known BMPs and GDFs to the cystine-knot-domain of human GDF-5 are listed in FIG. 4.

The results of an alkaline phosphatase assay (ALP) with recombinant human GDF-5 (rh-GDF-5) and hGDF-5 ML-mutant M453V/M456V (as described in example 2) are illustrated in FIG. 5.

FIG. 6 shows histological cross-sections (AlizarinRed-S staining of newly formed calcium) and µCT scans of growth factor-treated scaffolds 4 weeks after implantation in SCID mice according to example 3.

Figure 7:
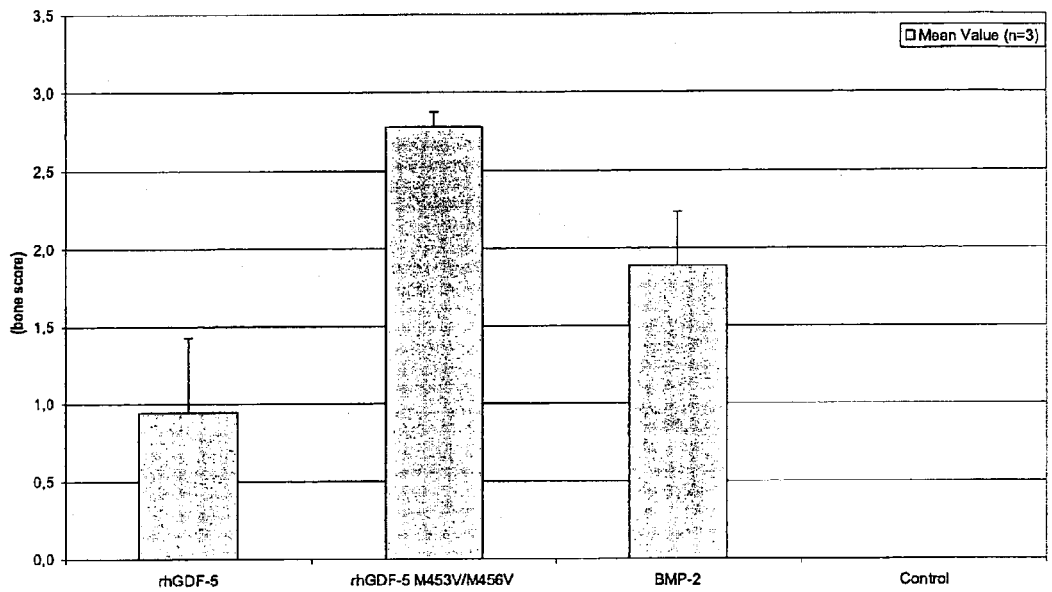
FIG. 7 shows an estimation of new bone formation on the scaffolds according to example 3 is made. In each group, three animals were examined (n=3) and a cumulative value determined.

An estimation of new bone formation on the scaffolds according to example 3 is made in FIG. 7. In each group, three animals were examined (n=3) and a cumulative value determined. The following scaling was used:

| | | |
|---|---|---|
| no | bone | 0 |
| 1-10% | bone | 1 |
| 10-50% | bone | 2 |
| 50-100% | bone | 3 |

Example 1

Creation, Expression and Purification of ML-Mutants

DNAs coding for the mature parts of human GDF-5, human GDF-6 and human GDF-7 proteins have been isolated from human ROB-C26 osteoprogenitor cells (Yamaguchi et al. 1991, Calcif. Tissue Int. 49, 221-225) via RT-PCR technique and subsequently ligated into prokaryotic plasmid vectors. In order to identify functionally important amino acid residues in the mature parts of GDF-5, -6 and -7, various single mutations have been introduced into these sequences via site directed mutagenesis. All individual mutations were created by using the QuickChange™ site-directed mutagenesis kit with the PfuTurbo™ DNA polymerase and the DPN I endonuclease from Stratagene according to the instruction manual of the manufacturer.

Using the bacterial strain W3110BP transformed with the plasmids and induced with IPTG, the proteins were expressed in inclusion bodies. These inclusion bodies were isolated using a homogenization buffer (25 mM Tris HCl pH 7.3, 10 mM EDTA NaOH pH 8, 8 M Urea) and wash buffer (1 M Urea, 20 mM Tris HCl, pH 8.3, 10 mM EDTA NaOH pH 8.0) according to standard procedures. Further purification was carried out on a reversed phase column Aquapore Octyl (Applied Biosys, (CV=7.8 ml) 100×10, 20µ, No 186470) with a gradient from 100% of Eluent A (0.1% TFA, HPLC $H_2O$) to 100% Eluent B (0.1% TFA, 90% $CH_3N$, HPLC $H_2O$) in 104 minutes (flow rate: 3 ml/min). After a western blot control, the fractions containing the mutant protein were pooled and lyophilized.

The mutant proteins were dissolved in dissolving buffer (6 M Guanidin HCl, 50 m M Tris, 150 mM NaCl, 3 mM DTT, pH=8.0), the protein concentration was exactly adjusted to 2.6 mg/ml and the pH was adjusted between 8 and 9. After 2 h incubation at room temperature, refolding buffer (1 M NaCl, 50 mM Tris, 5 mM EDTA, 1 mM GSSG, 2 mM GSH, 33 mM Chaps, pH=9.5) was added under gentle agitation to reach a final concentration of 0.16 mg/ml.

The solution was then incubated for 48 h at 22° C. and the refolding was stopped by changing the pH to 3-4 by adding 18% HCl. After centrifugation, the non-refolded monomer was separated from the dimer form by carrying out a second RP-HPLC under the same conditions. The fractions containing the dimerized protein were pooled, lyophilized and stored at −70° C.

Example 2

Measurement of the Biological Activity of ML-Mutants In Vitro by ALP Assay $1 \times 10^4$ cells of osteo-/chondroprogenitor cell line ATDC-5 were incubated overnight in 96-well plates in cell culture medium (alpha-MEM, Penicilline/Streptomycine, 2 mM L-glutamine, 10% FCS) at 37° C., 5% $CO_2$, $H_2O$-saturated. The next day, cells were stimulated with the GDF-5-related proteins and mutants thereof for 72 hrs with indicated ligand concentrations. The cells were subsequently washed with PBS (phosphate buffered saline). Cell lysis was performed in 100 µl alkaline lysis buffer 1 (0.1M glycine, pH 9.6, 1% NP-40, 1 mM $MgCl_2$, 1 mM $ZnCl_2$) for 1 h at room temperature. Then 100 µl alkaline lysisbuffer 2 was added (0.1M glycine, pH 9.6, 1 mM $MgCl_2$, 1 mM $ZnCl_2$+2 mg/ml PNPP). The plates were incubated at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction.

As an example, results (average values of 2 independent experiments) regarding hGDF-5 mutant M453V/M456V are shown in FIG. 5. The mutant protein exhibits a biological activity of 585.5% (at 133 ng/ml), 356.3% (at 400 ng/ml) and 236.3% (at 1200 ng/ml) of the activity of wildtype protein (rh-GDF-5) in this assay (average of multiple experiments). The minimal activity measured for the mutant at a single protein concentration and in a single experiment was 150% of the activity of the wild-type protein.

Example 3

Ectopic Bone Formation In Vivo

A SCID-Mouse Model for rhGDF-5, rhGDF-5 M453V/M456V and BMP-2

The improved bone inducing capabilities of ML-mutants of GDF-5 related proteins were also verified in vivo. Beta-tricalcium phosphate ceramics (chronOS®, Synthes/RMS Foundation) were used as biodegradable biomaterials with a size of 3×3×3.5 mm. Growth factors were dissolved in sodium acetate pH 4, as followed: rhGDF-5 in a concentration of 10 µg in 7 µl; rhGDF-5 M453V/M456V in a concentration of 10 µg in 9 µl and BMP-2 (Induct OS Wyeth® Lot-no., 20603) was first dissolved in sterile water in a concentration of 3 mg/ml and then dissolved in sodium acetate in a concentration of 10 µg in 7 µl. Controls were saturated with 7 µl sodium acetate. After coating the scaffolds were then dried for 10 minutes and stored at −20° Celsius. Before implantation, the scaffolds were loaded with 10 µl fibronectin. In this study, severe combined immunodeficient mice (SCID), (30+/−2 g) were used. Under general i.p. anaesthesia, one subcutaneous pocket were bluntly created through a one centimeter incision at the back. One loaded scaffold was inserted into the pocket. The wound was closed with single interrupted sutures. Animals were sacrificed after four weeks and scaffolds were harvested. Histology and µCT scans (µCT 80 SCANCO MEDICAL) were performed. For histology, scaffolds were embedded in paraffin wax and sections of 5 µm thickness were stained with AlizarinRed-S (0.5%) and Fast Green (0.04%) to demonstrate the new built calcium within the scaffolds.

Results are displayed in FIGS. 6 and 7. Controls had no sign of new ectopic bone formation. Scaffolds loaded with rhGDF-5 did show a medium amount of newly built bone with some bone formation on the scaffold. RhGDF-5 M453V/M456V had the highest value of newly bone formation. Scaffolds loaded with rhGDF-5 453V/M456V showed prominent bone on the scaffold. The scaffolds treated with BMP-2 showed prominent bone on the scaffolds but without being as homogeneous as the scaffolds loaded with rhGDF-5 453V/M456V. In summary, results confirmed that rhGDF-5 453V/M456V leads to strongly enhanced bone formation in this SCID mouse model.

The invention claimed is:

1. A method for promoting cartilage growth in a patient in need thereof, comprising administering to the patient an effective amount of a recombinant protein comprising an amino acid sequence at least 75% identical to the 102 amino acid cysteine-knot domain of GDF-5 or a fragment of said recombinant protein, wherein
   a) the amino acid at the position corresponding to methionine 453 (M453) of human wild-type GDF-5 (SEQ ID NO: 1) is alanine, valine or isoleucine, and/or
   b) the amino acid at the position corresponding to methionine 456 (M456) of human wild-type GDF-5 (SEQ ID NO: 1) is alanine, valine or isoleucine,
and further wherein the recombinant protein or the fragment of said recombinant protein has an improved biological activity of at least 120% when compared to the mature GDF-5 protein.

2. The method of claim 1, wherein said recombinant protein or the fragment of said recombinant protein is administered to said patient in a biodegradable biomembrane.

3. The method of claim 1, wherein said recombinant protein or the fragment of said recombinant protein is administered to said patient in and/or on a biodegradable matrix material or pharmaceutically acceptable carrier and/or diluent.

4. The method of claim 1, wherein said patient suffers from cartilage degeneration and/or destruction.

5. A method for promoting bone growth and/or spinal fusion in a patient in need thereof comprising administering to the patient an effective amount of a recombinant protein comprising an amino acid sequence at least 75% identical to the 102 amino acid cysteine-knot domain of GDF-5 or a fragment of said recombinant protein, wherein
   a) the amino acid at the position corresponding to methionine 453 (M453) of human wild-type GDF-5 (SEQ ID NO: 1) is alanine, valine or isoleucine, and/or
   b) the amino acid at the position corresponding to methionine 456 (M456) of human wild-type GDF-5 (SEQ ID NO: 1) is alanine, valine or isoleucine, and further wherein the recombinant protein or the fragment of said recombinant protein has an improved biological activity of at least 120% when compared to the mature GDF-5 protein.

6. The method of claim 5, wherein said patient suffers from osteoporosis.

7. The method of claim 5, wherein said recombinant protein or the fragment of said recombinant protein is administered to said patient in and/or on a biodegradable matrix material or pharmaceutically acceptable carrier and/or diluent.

8. The method of claim 5, wherein said recombinant protein or the fragment of said recombinant protein is administered to said patient in and/or on a calcium phosphate matrix.

9. The method of claim 5, wherein a) the amino acid at the position corresponding to methionine 453 (M453) of human wild-type GDF-5 (SEQ ID NO: 1) is valine, and b) the amino acid at the position corresponding to methionine 456 (M456) of human wild-type GDF-5 (SEQ ID NO: 1) is valine.

10. The method of claim 5, wherein said administering promotes cartilage growth in said patient.

11. The method of claim 5, wherein said patient suffers from an injury or disease of the patient's bone, cartilage, connective tissue, connective tissue attachment, tendon, ligament, spinal/intervertebral disk, meniscus, dental tissue, dentin, and/or periodontal ligament.

12. The method of claim 5, wherein said patient suffers from bone degeneration and/or destruction.

* * * * *